United States Patent [19]

Ghio et al.

[11] Patent Number: 5,474,760
[45] Date of Patent: Dec. 12, 1995

[54] METHOD OF INHIBITING OXIDANTS USING ALKYLARYL POLYETHER ALCOHOL POLYMERS

[75] Inventors: Andrew J. Ghio; Claude A. Piantadosi, both of Durham, N.C.; Thomas P. Kennedy, Richmond, Va.

[73] Assignee: Duke University, Durham, N.C.

[21] Appl. No.: 219,770

[22] Filed: Mar. 29, 1994

Related U.S. Application Data

[63] Continuation-in-part of Ser. No. 39,732, Mar. 30, 1993, abandoned.

[51] Int. Cl.$^6$ .......................... A61K 9/12; A61K 31/765
[52] U.S. Cl. ...................... 424/45; 424/78.37; 514/828; 514/851
[58] Field of Search .................................. 424/45, 78.37; 514/851, 828

[56] References Cited

PUBLICATIONS

Robert A. Greenwald, *CRC Handbook of Methods for Oxygen Radical Research;* Determination of HOCl Production by Micloperoxidase; p. 300 (1987).

Cantin et al.; *The Journal of Clinical Investigation, Inc.* Protection by Antibiotics agains Myeloperoxidase–dependent Cytotoxicity to Lung Ephithelial Cells in Vitro; vol. 91, pp. 38–45 (Jan., 1993).

Ramsey, et al. *The New England Journal of Medicine;* Efficacy of Aerosolized Tobramycin in Patients with Cystic Fibrosis; vol. 328 No. 24 pp. 1740–1746 (Jun. 17, 1993).

Vasconcellos, et al. *Science;* Reduction in Viscosity of Cystic Fibrosis Sputum in Vitro by Gelsolin; vol. 263, pp. 969–971 (Feb. 18, 1994).

*Primary Examiner*—Jyothsna Venkat
*Attorney, Agent, or Firm*—Richard E. Jenkins

[57] ABSTRACT

A method and medicament for the inhibition of oxidants comprising administering a treatment effective amount of alkylaryl polyether alcohol polymers to a chemical or biologic system in need thereof. The medicament is preferably administered by aerosolization into the mammalian respiratory system. The medicament may also be applied to the mammalian skin. Preferably, the medicament includes a physiologically acceptable carrier which may be selected from the group consisting of physiologically buffered saline, isotonic saline, normal saline, petrolatum based ointments and U.S.P. cold cream.

5 Claims, 5 Drawing Sheets

METHOD OF INHIBITING OXIDANTS USING ALKYLARYL POLYETHER ALCOHOL POLYMERS

RELATED APPLICATION(S)

This application is a continuation-in-part of applicants' application U.S. Ser. No. 039,732, filed Mar. 30, 1993, now abandoned.

BACKGROUND OF THE INVENTION

The present invention relates to use of alkylaryl polyether alcohol polymers as antioxidants to suppress certain oxidant chemical reactions that cause tissue injury and disease in mammals and plants.

Oxygen is life-giving to aerobic plants and animals who depend on it for energy metabolism. It can also be lethal to those same organisms when it is altered from its stable dioxygen ($O_2$) state to any one of three partially reduced species: a) the one electron reduced form superoxide anion ($O_2^-$); b) the two electron reduced form hydrogen peroxide ($H_2O_2$); or the deadly three electron reduced form hydroxyl radical ($\cdot OH$). In biologic systems $O_2^-$ and $H_2O_2$ are metabolic byproducts of a host of enzymes (oxygenases) that use oxygen as a cofactor. $H_2O_2$ is also produced from $O_2^-$ by the enzymatic action of superoxide dismutases. However, $\cdot OH$ is generally produced only when $O_2^-$ and $H_2O_2$ interact with transitional ions of metals such as iron and copper in dangerous cyclical redox reactions:

| | |
|---|---|
| $O_2^- + Fe^{3+}$ | $Fe^{2+} + O_2$ |
| $H_2O_2 + Fe^{2+}$ | $Fe^{3+} + \cdot OH + {}^-OH$ |

The above reaction is termed the superoxide driven Fenton reaction. The Fenton reaction can also be initiated by other reducing substances such as ascorbate in the presence of ferric iron and $H_2O_2$.

While $O_2^-$ and $H_2O_2$ are each toxic for biological systems, $\cdot OH$ (and its alternate hypothesized form the ferryl intermediate $FeO^{2+}$) is a highly reactive species that can oxidize unsaturated membrane lipids, damage cellular proteins and cause mutagenic strand breaks in DNA. To prevent injury from partially reduced $O_2$ species under normal conditions, cells have evolved an elaborate system of antioxidant enzymes (superoxide dismutase, catalase, glutathione peroxidase) and antioxidant molecules (glutathione, alpha-tocopherol, beta carotene). However, when production of partially reduced $O_2$ species exceeds the capacity of cellular antioxidant defenses to contain them, oxidant injury occurs. A growing number of mammalian disease entities are now thought to be related to overproduction of partially reduced $O_2$ species, including the reperfusion injury syndromes myocardial infarction and stroke, adult respiratory distress syndrome, oxygen toxicity of the lung, lung injury from asbestos, Parkinson's disease, thermal and solar burns of the skin, and injury to the gastrointestinal tract from nonsteroidal anti-inflammatory agents (see Table IV, page 60, Halliwell B and Gutteridge JMC. *Methods in Enzymology* (1990) 186:1–85). Also, studies suggest that airway cells in cystic fibrosis patients are at risk of oxidant-mediated injury. The reason is that the leukocyte-derived enzyme, myeloperoxidase, present in large amounts in the bronchial secretions of cystic fibrosis patients, converts with $H_2O_2$ produced by polymorphonuclear leukocytes to $HOCl/OCl$, the major leukocyte-derived oxidant. See, for instance, Cantin et al. "Protection by Antibiotics Against Myeloperoxidase-Dependent Cytotoxicity to Lung Epithelial Cells in Vitro," *Journal of Clinical Investigation* (January, 1993) 91:38–45; Ramsey et al., "Efficacy of Aerosolized Tobramycin in Patients with Cystic Fibrosis," *The New England Journal of Medicine* (June, 1993) 328:1740–1746; Vasconcellos et al., "Reduction In Viscosity of Cystic Fibrosis Sputum in Vitro by Gelsolin," *Science* (February, 1994) 263:969–971. Treatment of these conditions is increasingly directed either toward strategies that prevent enzymatic production of partially reduced $O_2$ species and to the introduction of exogenous antioxidant compounds that restore oxidant-antioxidant balance in biologic and chemical systems.

Antioxidants are compounds that can be easily oxidized to stable chemical forms. They can protect chemical and biologic systems by sacrificing themselves to oxidation in preference to oxidation of critically important chemical and biologic molecules. Not all oxidizable compounds can perform an antioxidant function. To successfully protect chemical and biologic systems from oxidants, the antioxidant must have a higher reactivity for the oxidant than the chemical or biologic molecule which it seeks to protect. It is theoretically possible to synthesize a multitude of compounds with antioxidant properties. However, the factor limiting use of these antioxidants as treatments in biologic systems is the inherent toxicity of the antioxidant compounds themselves. Thus, it is a major advantage to discover that a class of commonly used and nontoxic ingredients in medicinal pharmacologic preparations are also potent antioxidants. Not only can such compounds react with partially reduced $O_2$ species, but they can be used as treatments for oxidant mediated diseases without themselves causing toxicity to biologic systems.

SUMMARY OF THE INVENTION

As can be explained below, this invention describes how alkylaryl polyether alcohol polymers are useful as antioxidants in blocking oxidant reactions and biologic injury from partially reduced $O_2$ species. Alkylaryl polyether alcohol polymers are known and used commercially as surface active detergents and wetting agents (U.S. Pat. No. 2,454,541), the disclosure of which is incorporated herein by reference. All alkylaryl polyether alcohol polymers disclosed in this patent should work in the present invention.

A structure representative of the class of compounds is shown in FIG. 1. The best known of this class is tyloxapol, a polymer of 4-(1,1,3,3-tetramethylbutyl)phenol with formaldehyde and oxirane. Tyloxapol has been used in human pharmacologic formulations for over 30 years (Tainter ML et al. *New England Journal of Medicine* (1955) 253:764–767). Tyloxapol is relatively nontoxic and does not hemolyze red blood cells in a thousand times the concentrations at which other detergents are hemolytic (Glassman HN. *Science* (1950) 111:688–689).

It is the object of the present invention to provide a method to inhibit oxidant chemical reactions caused by partially reduced $O_2$ species.

It is a further object of the present invention to provide a method to protect mammalian tissues against injury from partially reduced $O_2$ species.

It is a further object of the present invention to provide a method and a medicament for the treatment of cystic fibrosis in patients having the disease to protect the patients from airway injury by $HOCl/OCl$, which for convenience, is referred to herein also as HOCl.

It is a further object of the present invention to provide a method for inhibiting oxidant chemical reactions caused by partially reduced $O_2$ species by aerosol treatment with the therapeutic agent.

It is a further object of the present invention to provide a method for inhibiting oxidant chemical reactions caused by partially reduced $O_2$ species by topical application of the therapeutic agent to the skin.

It is an advantage of the present invention that the therapeutic agent is produced from a toxicologically characterized class of compounds with low toxicologic potential to biologic systems.

Consideration of the specification, including the several figures and examples to follow will enable one skilled in the art to determine additional objects and advantages of the invention.

The present invention provides a medicament for the inhibition of injurious effects of partially reduced $O_2$ species in chemical and biologic systems comprising a treatment effective amount of tyloxapol and related alkylaryl polyether alcohol polymers. In preferred embodiments of the invention, the medicament is directly instilled into the respiratory system and administered by aerosolization. In this embodiment, the medicament preferably includes a physiologically acceptable carrier which may be selected from the group consisting of physiologically buffered saline, isotonic saline, and normal saline and an additional treatment effective amount of cetyl alcohol. The pH of the alkylaryl polyether alcohol polymer and carrier mixture is preferably greater than 6.5 but equal to or less than 7.4. In other preferred embodiments of the invention, the medicament is applied topically to the skin. In this embodiment, the medicament preferably includes a physiologic carrier selected from a commercially available petrolatum based ointment or U.S.P. cold cream.

BRIEF DESCRIPTION OF THE DRAWINGS

Reference to the following detailed description may help to better explain the invention in conjunction with the drawings which.

DETAILED DESCRIPTION OF THE INVENTION

Figure 1:
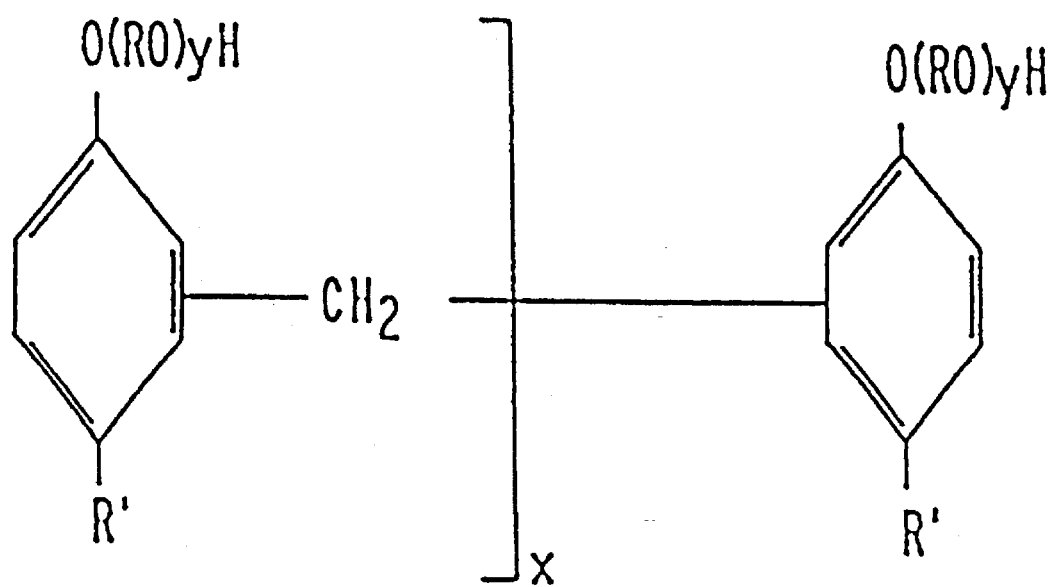
FIG. 1 shows the proposed structure of the class of compounds known as alkylaryl polyether alcohol polymers wherein R=ethylene; $R^1$=tertiary octyl; x is greater than 1; and y=8 to 18.

Alkylaryl polyether alcohol polymers can in general be synthesized by condensing alkylaryl alcohols with formaldehyde, as described by Bock and Rainey in U.S. Pat. No. 2,454,541 (1948 to Rohm & Haas). Several specific alkylaryl polyether alcohol polymers can be easily synthesized by methods previously described (J. W. Conforth et al. *Nature* (1951) 168:150–153). The prototype compound of this class tyloxapol can be conveniently purchased in pharmacologically acceptable purity from Rohm and Haas Co., Philadelphia, Pa.

For treatment of mammalian respiratory conditions related to overproduction of partially reduced $O_2$ species, the alkylaryl polyether alcohol polymer is dissolved in sterile 0.9% NaCl for injection, and the pH is adjusted to approximately 7.0 by addition of NaOH or HCl. A nonpolymeric alkyl or aryl alcohol such as cetyl alcohol (hexadecanol) may be added equivalent to 1–1.5 times the weight of tyloxapol to increase the effectiveness of the mixture in protection against oxidant injury. This mixture is then administered to the lung by direct instillation into the respiratory system. The mixture may also be administered by aerosolization using a clinically available positive pressure driven nebulizer that produces respirable particles of less than 5 microns mass median diameter. As an example, a 0.125% solution of tyloxapol is made in sterile 0.9% NaCl and double glass distilled deionized water to make it isotonic with respect to respiratory secretions. The pH is adjusted to approximately 7.0 to prevent bronchospasm from extremes of acidity or alkalinity. This mixture is sterilized by vacuum filtration through a 0.22 micron Millipore filter and 3.3 ml each is packaged into 5 ml unit dose glass vials with rubber stoppers fastened with aluminum crimp-on "flip-tear" seals. To provide additional sterilization of product, unit dose vials are terminally autoclaved 12–14 minutes at 125 degrees Centigrade. A 5% concentration of glycerol may be optionally added to the above mixture to stabilize droplet size during aerosolization. For administration of treatment effective doses, 3 ml of sterile tyloxapol solution is inhaled as an aerosol every 4–6 hours using a clinically available positive pressure driven nebulizer (Acorn or deVilbiss). Alternatively, the mixture can be nebulized into the respiratory delivery circuit of a mechanical ventilator. A beta sympathetic agonist bronchodilator (such as 1.25 to 2.5 mg of albuterol) can be mixed with the tyloxapol solution and nebulized concomitantly to prevent any transient bronchospasm that might occur from the tyloxapol solution itself.

For treatment of cutaneous oxidant-mediated disorders such as solar burn, a 0.5 to 5% mixture (w/w) is made with an alkylaryl polyether alcohol such as tyloxapol in a commercially available petrolatum based ointment such as Aquaphor (Beiersdorf, Inc., Norwalk, Conn.), white petrolatum or U.S.P. cold cream as the base vehicle. This mixture is rubbed lightly onto the affected skin area 3 to 4 times daily.

In order to facilitate a further understanding of the invention, the following examples primarily illustrate certain more specific details thereof.

Example I demonstrates the potent activity of alkylaryl polyether alcohol polymers as ·OH inhibitors in chemical systems. Example II demonstrates the therapeutic benefit of using alkylaryl polyether alcohol polymers to prevent mammalian lung injury from exposure to 100% oxygen. Example III demonstrates the potent activity of alkylaryl polyether alcohol polymers as scavengers of HOCl in chemical systems.

EXAMPLE I

Inhibitions of Oxidants Generated by the Fenton Reaction

Figure 2:
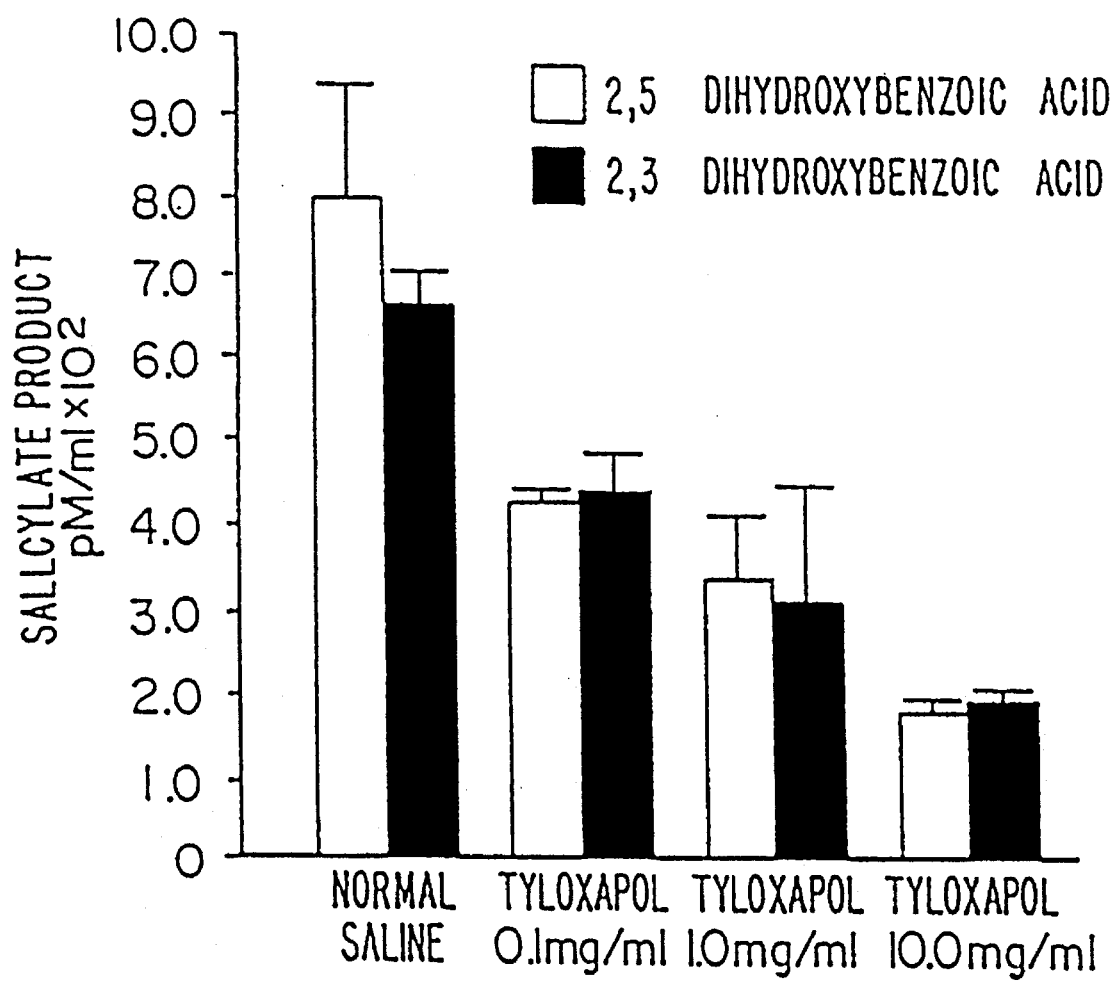
FIG. 2 shows a graph of the inhibitory effect of tyloxapol on .OH generation by the Fenton reaction, as measured by hydroxylation of salicylate.

The first chemical system used to test the antioxidant activity of alkylaryl polyether alcohol polymers employed salicylate as the target molecule of oxidants. Hydroxyl radical reacts with salicylic acid (2-hydroxybenzoic acid) to produce two dihydroxybenzoic acid products, 2,3- and 2,5-dihydroxybenzoic acid. These hydroxylated products provide evidence of ·OH generation (R. A. Floyd et al. *Journal of Biochemical and Biophysical Methods* (1984) 10:221–235; R. A. Floyd et al. *Journal of Free Radicals in Biology & Medicine* (1986) 2:13–18). The detection of 2,3- and 2,5-dihydroxybenzoic acid was performed using high performance liquid chromatography with electrochemical detection. Suspensions of 10 uM $FeCl_3$, 1.0 mM $H_2O_2$, 1.0 mM ascorbate, and 10.0 uM salycylic acid were employed to generate and detect ·OH. Either 0.1 ml of normal saline or tyloxapol (final concentrations of 0.0 to 10 mg/ml) were added. The reaction mixtures were incubated at 45 degrees Centigrade for 30 min and centrifuged at 1200 g for 10 min. Supernatant was centrifuged (Beckman Microfuge E) through a 0.22 uM microfuge tube filter (PGC Scientific No. 352-118) at 15,000 g. A 100 uL sample of the eluate was injected onto a C18 RP HPLC column (250×4.7 mm, Beckman No. 235329). Hydroxylated products of salicylate were quantified with a Coulochem electrochemical detector (ESA model 5100A) with the detector set at a reducing potential of −0.40 VDC. The guard cell (used as a screen) was set at an oxidizing potential of +0.40 VDC. Measurements were done in duplicate. FIG. 2 shows that the addition of tyloxapol to the reaction mixture inhibited ·OH generation in a concentration dependent manner.

Figure 3:
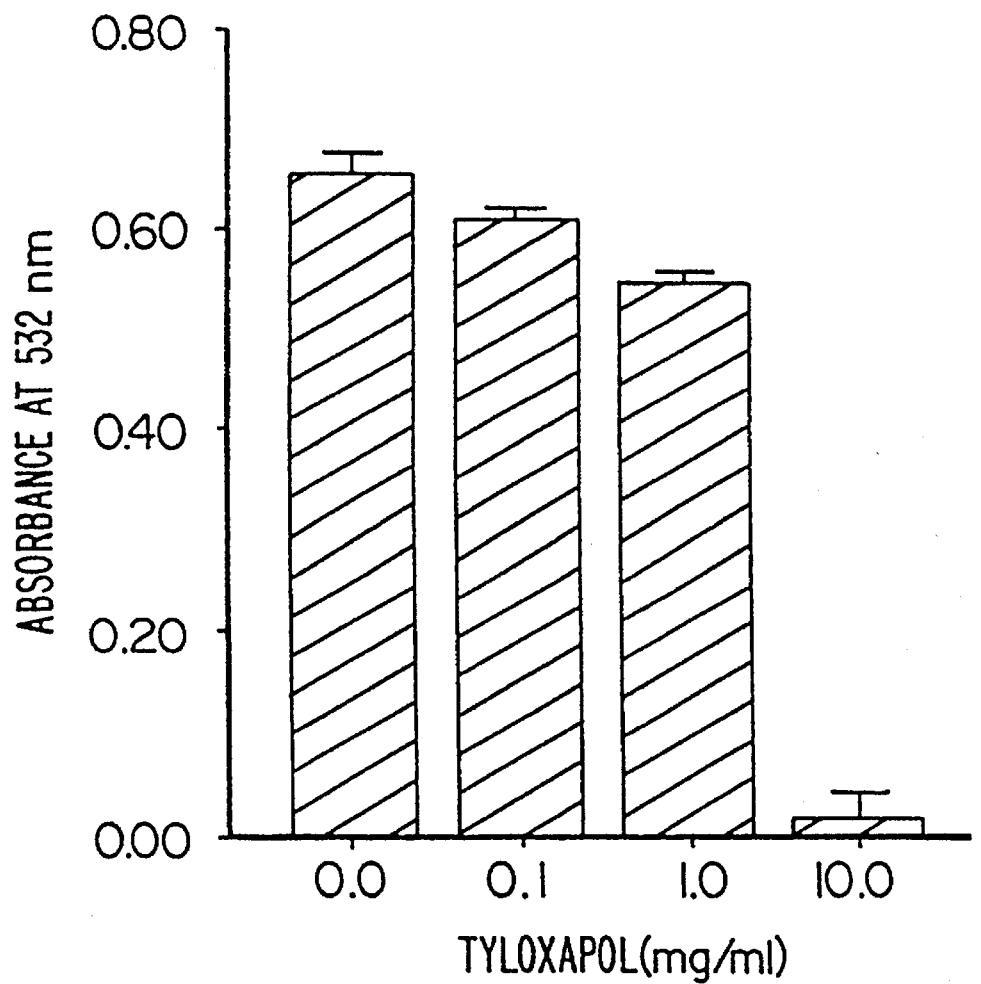
FIG. 3 shows a graph of the inhibitory effect of tyloxapol on ·OH generation by the Fenton reaction, as measured by oxidation of the sugar 2-deoxyribose.

The second chemical system used to test the antioxidant activity of alkylaryl polyether alcohol polymers employed 2-deoxyribose as the target molecule of oxidants. This pentose sugar reacts with oxidants to yield a mixture of products. On heating with thiobarbituric acid (TBA) at low pH, these products form a pink chromophore that can be measured by its absorbance at 532 nm (B. Halliwell and J. M. C. Gutteridge. *Methods in Enzymology* (1990) 186:1–85). The chemical system employed to generate oxidants was a reaction mixture containing 10.0 uM $FeCl_3$, 1.0 mM ascorbate, 1.0 mM $H_2O_2$, and 1.0 mM deoxyribose in Hanks Balanced Salt Solution. This system is useful for measuring site-specific ·OH generation on biologic molecules, as described by Halliwell and Gutteridge in the reference immediately above. Either 0.1 ml of normal saline or tyloxapol (final concentrations of 0.0 to 10.0 mg/ml) were added. The reaction mixtures were incubated at 45 degrees Centigrade for 30 min and centrifuged at 1200 g for 10 min. One ml of both 1.0% (w/v) TBA and 2.8% (w/v) trichloroacetic acid were added to 1.0 ml of supernatant, heated at 100 degrees Centigrade for 10 min, cooled in ice, and the chromophore determined in triplicate by its absorbance at 532 nm. FIG. 3 shows that the addition of 10 mg/ml tyloxapol to the reaction mixture causes marked inhibition of the oxidation of deoxyribose, as measured by absorbance of the oxidant reaction produced at 532 nm.

The third system used to test the antioxidant activity of alkylaryl polyether alcohol polymers employed asbestos as the source of iron for oxidant generation and 2-deoxyribose as the target molecule of oxidants. The generation of oxidants by asbestos has been described previously (A. J. Ghio et al. *American Journal of Physiology (Lung Cellular and Molecular Physiology 7)* (1992) 263:L511–L518). The reaction mixture, in a total volume of 2.0 ml phosphate-buffered saline (PBS), contained the following reagents: 1.0 mM deoxyribose, 1.0 mM $H_2O_2$, 1.0 mM ascorbate, and 1.0 mg/ml crocidolite asbestos. The mixture was incubated at 37 degrees Centigrade for 1 h with agitation and then centrifuged at 1,200 g for 10 min. Oxidant generation was assessed by measuring TBA reactive products of deoxyribose as detailed in the paragraph above. Measurements were done in triplicate. TABLE I below shows that the addition of tyloxapol inhibited in a concentration dependent manner the generation of oxidants by asbestos, as measured by absorbance of the oxidant reaction product at 532.

TABLE I

| Effect of Tyloxapol on Oxidant Generation by Asbestos | |
|---|---|
| | Absorbance at 532 nm |
| Tyloxapol 0.0 mg/ml | 0.93 ± 0.02 |
| Tyloxapol 0.1 mg/ml | 0.89 ± 0.04 |
| Tyloxapol 1.0 mg/ml | 0.75 ± 0.01 |
| Tyloxapol 10.0 mg/ml | 0.53 ± 0.04 |

EXAMPLE II

Protection from Mammalian Lung Injury by 100% Oxygen

To determine if alkylaryl polyether alcohol polymers could protect against oxidant injury to intact biologic systems, this treatment was studied in a well established model of oxygen toxicity to the lung (J. F. Turrens et al. *Journal of Clinical Investigation* (1984) 73:87–95). Sixty-day old male Sprague-Dawley rats (Charles River, Inc., Wilmington, Mass.) were tracheally instilled with 0.5 ml of either normal saline, tyloxapol (6.0 mg) or tyloxapol (6.0 mg) and cetyl alcohol (hexadecanol, 11.0 mg). These rats (n=10 in each treatment group) were then exposed to either air or 100% oxygen in plexiglass chambers at a flow rate of 10 liters/min. Oxygen percentage was monitored by a polarographic electrode and maintained continuously above 98%. Temperature was maintained between 20 and 22 degrees Centigrade. Survival times were determined by checking animals every 4 hours. Separate groups of rats treated similarly (n=10 in each treatment group) were exposed to 100% oxygen for 61 hours, and then were euthanized with 100mg/kg intraperitoneal pentobarbital. Pleural fluid volume was measured by aspirating pleural fluid from the chest cavity through a small incision in the diaphragm. Lung wet/dry weight ratios were calculated from the left lung after drying the tissue for 96 hours at 60 degrees Centigrade. Survival data in shown TABLE II below. Rats receiving intratracheal tyloxapol had markedly improved survival compared to placebo control animals instilled with saline. The protective effect of tyloxapol was further enhanced by combining it with cetyl alcohol.

TABLE II

| Effect Of Tyloxapol On Oxygen Toxicity In Rats | | | |
|---|---|---|---|
| | Percent Survival | | |
| Hours | Saline | Tyloxapol | Tyloxapol/Cetyl Alcohol |
| 0 | 100 | 100 | 100 |
| 58 | 100 | 100 | 100 |
| 62 | 83 | 100 | 100 |
| 66 | 42 | 100 | 100 |
| 70 | 17 | 75 | 100 |
| 72 | 17 | 75 | 100 |
| 76 | 8 | 58 | 100 |
| 80 | 8 | 58 | 100 |
| 84 | 8 | 58 | 100 |
| 88 | 8 | 58 | 100 |
| 92 | 0 | 58 | 100 |
| 96 | 0 | 58 | 100 |

Figure 4:
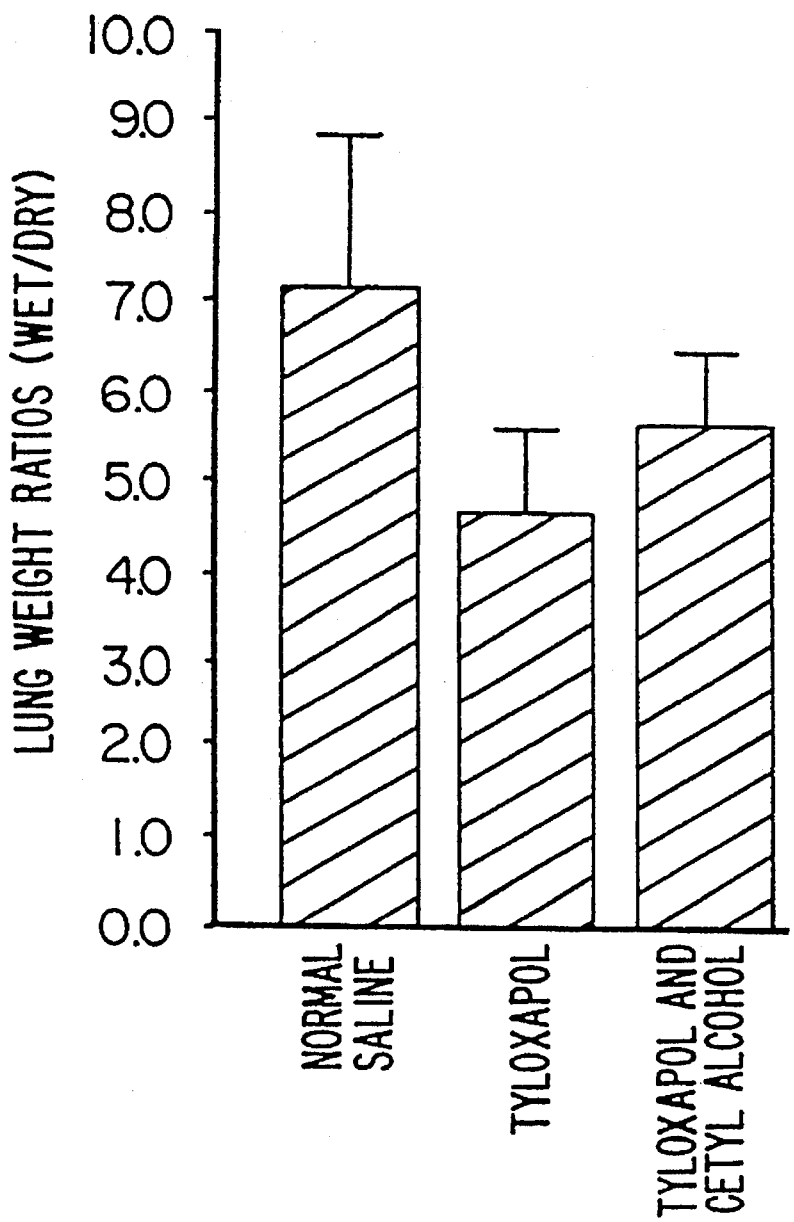
FIG. 4 shows lung wet/dry weight ratios in rats exposed to 100% oxygen and treated with normal saline, tyloxapol, and tyloxapol plus cetyl alcohol.
Figure 5:
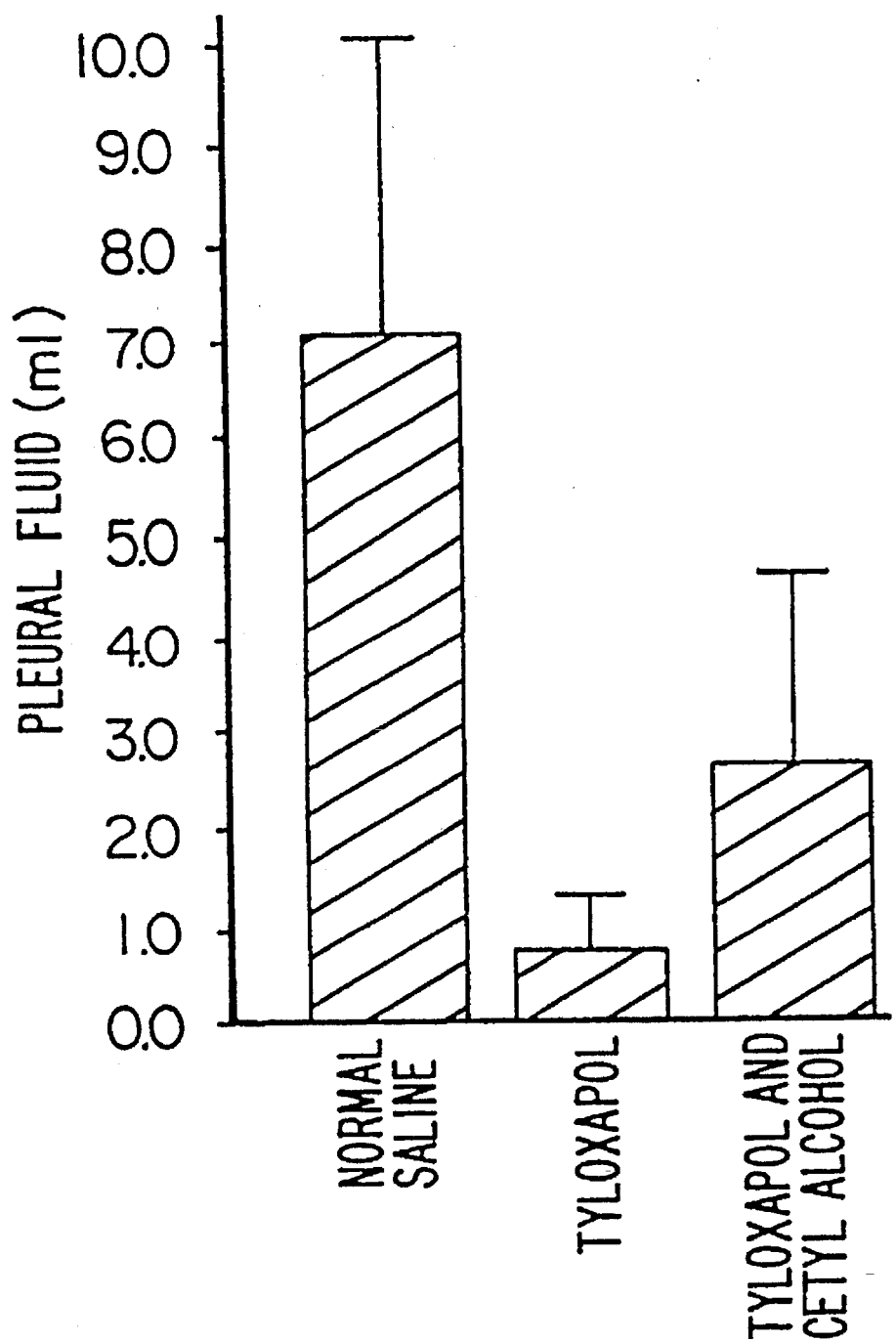
FIG. 5 shows pleural fluid in rats exposed to 100% oxygen and treated with normal saline, tyloxapol, and tyloxapol plus cetyl alcohol.

Lungs wet/dry weight ratios were substantially lower in rats treated with tyloxapol or tyloxapol and cetyl alcohol (FIG. 4), demonstrating that tyloxapol or the combination of tyloxapol and cetyl alcohol protect against edema formation from oxidant injury. Rats treated with tyloxapol or the combination of tyloxapol and cetyl alcohol also had less pleural fluid accumulation than saline treated controls (FIG. 5). These results demonstrate the ability of alkyaryl polyether alcohol polymers such as tyloxapol to protect against oxidant tissue injury. The survival studies (TABLE II) further demonstrate that the protective effect of the medicament is enhanced by combining it with alcohols such as cetyl alcohol.

EXAMPLE III

Scavenging of HOCl

The activity of tyloxapol to scavenge $OCl^{-1}$ was tested studying its ability to prevent $OCl^{-1}$-medicated oxidant conversion of diethanolamine to its corresponding chloramine ("Determination of HOCl Production by Micloperoxidase" Robert A Greenwald, editor, *Handbook of Methods for Oxygen Radical Research*, CRC Press, Boca Raton, Fla. (1987), page 300). The reaction mixture comprised 0.9 ml of 10.0mM diethanolamine in 0.1M sodium acetate buffer, pH of 4.5. To this resultant was added either 100 microliters of 0.1M NaCl or tyloxapol in 0.1M NaCl, and the baseline absorbance was read at 280 nm. NaOCl was added to a final concentration of 10 mM. The reaction mixture was incubated 15 minutes, and the absorbance was measured at 280 nm. The difference in 80 before and after addition of NaOCl was used as a measure of concentration of the stable chloramine. Experiments were performed in triplicate. Results are summarized in Table III below.

TABLE III

| Microliters of Tyloxapol (10 mg/ml) | Absorbance (Mean ± SD) |
|---|---|
| 0 | 0.505 ± 0.002 |
| 25 | 0.468 ± 0.008 |
| 50 | 0.444 ± 0.023 |
| 75 | 0.377 ± 0.010 |

TABLE III-continued

| Microliters of Tyloxapol (10 mg/ml) | Absorbance (Mean ± SD) |
|---|---|
| 100 | 0.319 ± 0.025 |

Thus, tyloxapol is a potent inhibitor of the oxidant activity of HOCl, and should be useful in preventing HOCl-medicated oxidant injury of the airway in diseases such as cystic fibrosis. Administration of tyloxapol by tracheal installation to cystic fibrosis patients should inhibit HOCl produced in these patients and therefore protect them from oxidant injury. The result should be even better if some cetyl alcohol is admixed with the tyloxapol; preferably, the cetyl alcohol is added in 1 to 1.5 times the weight of the tyloxapol. Preparation of samples for administration to the patient should be the same as described above in the second paragraph of the "DETAILED DESCRIPTION OF THE INVENTION" section herein, most preferably inhalation of 3 ml of a 0.125% solution of tyloxapol by jet aerosol every 4 to 6 hours.

The appended claims set forth various novel and useful features of the invention.

What is claimed is:

1. A method for the treatment of cystic fibrosis diesease resultant from overproduction of HOCl, said method comprising administering to a mammal having cystic fibrosis disease an effective amount of tyloxapol to inhibit oxidant chemical reactions caused by the HOCl in the mammal.

2. The method of claim 1, wherein said administering comprises administering the tyloxapol directly into the mammal's respiratory tract.

3. The method of claim 1, wherein said administering comprises administering the tyloxapol by aerosolization.

4. The method of claim 1, wherein said administering of the tyloxapol comprises a physiologically acceptable carrier.

5. The method of claim 4, wherein said physiologically acceptable carrier is selected from the group consisting of isotonic saline, normal saline, and combinations thereof.

* * * * *

UNITED STATES PATENT AND TRADEMARK OFFICE
CERTIFICATE OF CORRECTION

PATENT NO. : 5,474,760

DATED : December 12, 1995

INVENTOR(S) : Ghio et al.

Page 1 of 2

It is certified that error appears in the above-identified patent and that said Letters Patent is hereby corrected as shown below:

At the last line of column 1 on the Title page, in item [56] on the front page, change "Micloperoxidase" instead to read as -- Myeloperoxidase --.

At line 1 of column 2 on the front page, in item [56] on the front page, delete ", Inc." and replace with -- ; --.

At line 2 of column 2 on the front page, in item [56] on the front page, delete "agains" and replace with -- against --.

At line 12 of column 5, delete "salycylic" and replace with -- salicylic --.

At line 17 of column 7, delete "$OCl^{-1}$" and replace with -- HOCl --.

At line 18 of column 7, delete "$OCl^{-1}$-medicated" and replace with -- HOCl-mediated --.

UNITED STATES PATENT AND TRADEMARK OFFICE
CERTIFICATE OF CORRECTION

PATENT NO. : 5,474,760

DATED : December 12, 1995

INVENTOR(S) : Ghio et al.

It is certified that error appears in the above-identified patent and that said Letters Patent is hereby corrected as shown below:

At line 20 of column 7, delete "Micloperoxi-" and replace with -- Myeloperoxi- --.

At line 21 of column 7, delete "Robert A " and replace with --, Robert A. --.

At line 10 of column 8, delete "cated" and replace with -- ated --.

Signed and Sealed this

Ninth Day of April, 1996

BRUCE LEHMAN

*Attest:*

*Attesting Officer*  Commissioner of Patents and Trademarks